US012661057B2

(12) United States Patent
Kayser et al.

(10) Patent No.: US 12,661,057 B2
(45) Date of Patent: Jun. 23, 2026

(54) AUTOMATICALLY IDENTIFYING PRESSURE INJURIES

(71) Applicant: Hill-Rom Services, Inc., Batesville, IN (US)

(72) Inventors: Susan A. Kayser, Batesville, IN (US); Eugene G. Urrutia, Apex, NC (US); Karrie Ann Schwencer, Cary, NC (US); Sinan Batman, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 946 days.

(21) Appl. No.: 17/487,663

(22) Filed: Sep. 28, 2021

(65) Prior Publication Data

US 2022/0095999 A1 Mar. 31, 2022

Related U.S. Application Data

(60) Provisional application No. 63/084,518, filed on Sep. 28, 2020.

(51) Int. Cl.
*G16H 40/67* (2018.01)
*A61B 5/00* (2006.01)
(Continued)

(52) U.S. Cl.
CPC ............ *A61B 5/447* (2013.01); *A61B 5/4866* (2013.01); *A61B 5/6892* (2013.01);
(Continued)

(58) Field of Classification Search
CPC ..... A61B 5/447; A61B 5/4866; A61B 5/6892; A61B 5/7267; A61B 5/7275;
(Continued)

(56) References Cited

U.S. PATENT DOCUMENTS 9,320,665 B2 4/2016 Main et al.
9,861,550 B2 * 1/2018 Ribble ................... G16H 20/40
(Continued)

FOREIGN PATENT DOCUMENTS

CN 107348942 A 11/2017
CN 206612902 U 11/2017
(Continued)

OTHER PUBLICATIONS

I. Cho, I. Park, E. Kim, E. Lee, D. W. Bates, "Using EHR data to predict hospital-acquired pressure ulcers: A prospective study of a Bayesian Network model," 2013 Int'al Journal of Medical Informatics 82 (2013) pp. 1059-1067 (Year: 2013).*
(Continued)

*Primary Examiner* — Devin C Hein
*Assistant Examiner* — Vincent C Ilagan
(74) *Attorney, Agent, or Firm* — Lee & Hayes, P.C.

(57) ABSTRACT

Various systems, devices, and methods for predicting and identifying root causes of pressure injuries in a clinical environment are described. An example method includes identifying, based on an electronic medical record (EMR) of a patient, that the patient has an injury; receiving, from one or more sensors, sensor data indicating one or more parameters of the patient; determining, based on the sensor data, at least one root cause of the injury; and transmitting, to an external computing device, a report indicating the at least one root cause of the injury.

11 Claims, 7 Drawing Sheets

(51) Int. Cl.
    *G16H 10/60*         (2018.01)
    *G16H 50/30*         (2018.01)

(52) U.S. Cl.
    CPC .......... *A61B 5/7267* (2013.01); *A61B 5/7275*
        (2013.01); *A61B 5/7282* (2013.01); *G16H*
        *10/60* (2018.01); *G16H 40/67* (2018.01);
        *G16H 50/30* (2018.01); *A61B 5/0002*
        (2013.01)

(58) Field of Classification Search
    CPC ...... A61B 5/7282; G16H 10/60; G16H 40/67;
        G16H 50/20; G16H 50/30; G16H 80/00
    See application file for complete search history.

(56) References Cited

U.S. PATENT DOCUMENTS

| | | | |
|---|---|---|---|
| 10,117,617 | B2 | 11/2018 | Cantu et al. |
| 10,387,720 | B2 | 8/2019 | Johnson et al. |
| 10,426,396 | B2 | 10/2019 | Achenbruch et al. |
| 10,496,788 | B2 | 12/2019 | Amarasingham et al. |
| 10,600,204 | B1 | 3/2020 | Rush et al. |
| 10,624,585 | B2 | 4/2020 | Fleischer et al. |
| 10,631,732 | B2 | 4/2020 | Larson et al. |
| 10,682,090 | B2 | 6/2020 | Johnson et al. |
| 10,874,330 | B2 * | 12/2020 | Larson ................. A61B 5/0205 |
| 2004/0059199 | A1 | 3/2004 | Thomas et al. |
| 2011/0068939 | A1 | 3/2011 | Lachenbruch |
| 2013/0249695 | A1 | 9/2013 | Hann |
| 2013/0317399 | A1 * | 11/2013 | Ribble ................... G16H 20/30 |
| | | | 601/84 |
| 2015/0109442 | A1 | 4/2015 | Derenne |
| 2016/0278692 | A1 * | 9/2016 | Larson ................. A61B 5/0205 |
| 2017/0228507 | A1 * | 8/2017 | Bottinger .............. G16B 40/00 |
| 2017/0245799 | A1 | 8/2017 | Fleischer et al. |
| 2017/0360357 | A1 | 12/2017 | Larson et al. |
| 2018/0068179 | A1 | 3/2018 | Derenne et al. |
| 2019/0021650 | A1 * | 1/2019 | Lee ...................... A61B 5/0004 |
| 2019/0104982 | A1 * | 4/2019 | Dunn ................... A61B 5/7264 |
| 2019/0125248 | A1 * | 5/2019 | Curtin ................. A61B 5/1455 |
| 2019/0307405 | A1 | 10/2019 | Terry et al. |
| 2020/0043579 | A1 * | 2/2020 | McEwing ............. G06F 40/151 |
| 2020/0043607 | A1 | 2/2020 | Zerhusen et al. |
| 2020/0155059 | A1 | 5/2020 | Kayser et al. |
| 2020/0163843 | A1 * | 5/2020 | Francis .................. G16H 10/60 |
| 2020/0405217 | A1 * | 12/2020 | Jayaraman ............... A61G 5/10 |
| 2021/0008413 | A1 * | 1/2021 | Asikainen ............ G06F 3/0304 |
| 2021/0249110 | A1 * | 8/2021 | Malvankar ............ G16H 10/60 |

FOREIGN PATENT DOCUMENTS

| | | | | |
|---|---|---|---|---|
| CN | 110931134 | A | 3/2020 | |
| CN | 111195180 | A | 5/2020 | |
| EP | 2667313 | A2 | 11/2013 | |
| EP | 3653110 | A1 | 5/2020 | |
| TW | 201802761 | A | 1/2018 | |
| WO | WO-2004093824 | A2 * | 11/2004 | ............ A23L 33/10 |
| WO | WO2014113897 | A1 | 7/2014 | |
| WO | WO2014149392 | A1 | 9/2014 | |
| WO | WO2015074007 | A1 | 5/2015 | |
| WO | WO-2019178583 | A1 * | 9/2019 | ............ A61B 5/447 |
| WO | WO2020037244 | A1 | 2/2020 | |

OTHER PUBLICATIONS

G. Matar, J. Lina, G. Kaddoum, "Artificial Neural Network for in-Bed Posture Classification Using Bed-Sheet Pressure Sensors," IEEE Journal of Biomedical and Health Informatics, vol. 24, No. 1, Jan. 2020, pp. 101-110. (Year: 2020).*

R. Yousefi et al., "A smart bed platform for monitoring & Ulcer prevention," 2011 4th International Conference on Biomedical Engineering and Informatics (BMEI), Shanghai, China, 2011, pp. 1362-1366, doi: 10.1109/BMEI.2011.6098589 (Year: 2011).*

Chinese Second Office Action mailed May 28, 2024 for Chinese Patent Application No. 202111144241.X, a foreign counterpart to U.S. Appl. No. 17/487,663, 19 pages.

Chinese Office Action mailed Sep. 26, 2023 for Chinese Patent Application No. 202111144241.X, a foreign counterpart to U.S. Appl. No. 17/487,663, 22 pages.

Extended European Search Report mailed Mar. 16, 2022 for European Patent Application No. 21199073.4, 11 pages.

Office Action for European Application No. 21199073.4, dated Mar. 27, 2026, 5 pages.

* cited by examiner

200

FIRST
CLINICAL
DEVICE
128-1

NTH
CLINICAL
DEVICE
128-N

ALERT(S)
AND/OR
REPORT(S)
208

IDENTIFICATION
SYSTEM
120

COMPUTING
MODEL
130

CLINICAL
DATA
202

SENSOR
DATA
206

EMR
DATA
204

FIRST
SUPPORT
DEVICE
104-A

MTH
SUPPORT
DEVICE
104-M

ELECTRONIC MEDICAL
RECORD (EMR)
SYSTEM
122

DATASTORE
124

IDENTIFY SENSOR DATA AND/OR EMR DATA OF FIRST
PATIENTS
402

IDENTIFY WHETHER THE FIRST PATIENTS DEVELOPED
PRESSURE INJURIES
404

TRAIN A COMPUTING MODEL TO PREDICT A PRESSURE
INJURY OF A SECOND PATIENT
406

IDENTIFY SENSOR DATA OF A PATIENT
502

IDENTIFY EMR DATA OF THE PATIENT
504

CALCULATE A SCORE INDICATIVE OF A RISK THAT THE
PATIENT HAS OR WILL DEVELOP A PRESSURE INJURY BASED
ON THE SENSOR DATA AND THE EMR DATA
506

OUTPUT AN ALERT BASED ON THE SCORE
508

600

IDENTIFY THAT A PATIENT HAS DEVELOPED A PRESSURE
INJURY
602

IDENTIFY SENSOR DATA AND/OR EMR DATA OF THE
PATIENT
604

IDENTIFY ONE OR MORE ROOT CAUSES OF THE PRESSURE
INJURY BASED ON THE SENSOR DATA AND/OR THE EMR
DATA
606

OUTPUT A REPORT INDICATING THE ROOT CAUSE(S)
608

AUTOMATICALLY IDENTIFYING PRESSURE INJURIES

CROSS-REFERENCE TO RELATED APPLICATION

This application claims the priority of U.S. Provisional Application No. 63/084,518, which was filed on Sep. 28, 2020 and is incorporated by reference herein in its entirety.

TECHNICAL FIELD

This application relates generally to predicting and/or identifying pressure injuries experienced by patients in a hospital environment. In some cases, the root causes of pressure injuries can be derived.

BACKGROUND

Care facilities, such as hospitals, hospices, and the like, may manage numerous patients using a handful of care providers. For example, a hospital may have hundreds or even thousands of patients residing in in-patient wards, intensive care units (ICUs), and the like. These patients are managed by various care providers, including nurses, medical technicians, physician assistants, physicians, residents, fellows, and medical students.

Patients may develop pressure injuries in a care facility due to pressure and/or friction between skin and other objects. For example, an immobile patient may develop a pressure injury due to pressure between the patient and a bed on which the patient is resting. In some cases, a patient in contact with a medical device (e.g., an oxygen cannula or tubing) may develop a pressure injury due to pressure and/or friction between the skin of the patient and the medical device. Additionally, various risk factors increase the risk of developing a pressure injury. For example, the presence of moisture on the skin of the patient can increase the patient's risk of developing a pressure injury.

Care facilities have a significant incentive to prevent patients from developing pressure injuries. Pressure injuries can cause substantial discomfort to patients, and in some instances, can expose patients to secondary infections that can be deadly. Furthermore, medical insurers and reimbursement agencies will not pay a care facility for expenses associated with treating a pressure injury that developed while the patient was being cared for by the care facility. Care facilities generally have policies that prevents or ameliorates risk factors associated with developing pressure injuries. For example, care providers may encourage the patient to move around or shift position on a periodic basis in order to prevent pressure injuries from developing. However, in complex care environments, pressure injuries may still occur while patients are residing in care facilities.

When a pressure injury is identified on a patient, the patient may be referred to a wound care specialist. Wound ostomy catheter nurses (WOCNs), for example, are specialists that can diagnose the severity of a pressure injury and treat the pressure injury. However, if other care providers are slow to diagnose the pressure injury, even specialists may find the pressure injury difficult to treat. In severe cases, delays with diagnosing and/or treating a pressure injury can cause permanent deficits in the patient.

SUMMARY

Various implementations of the present disclosure relate to systems, devices, and methods for identifying or predicting pressure injuries. In various examples, at least one sensor can detect one or more parameters of a patient. The patient may be resting on a support structure, such as a hospital bed, that may cause the patient to develop a pressure injury. Furthermore, an electronic medical record (EMR) of the patient may track one or more parameters of the patient, such as nutrition levels of the patient. In some cases, data from the sensor(s) and/or the EMR can be analyzed in order to predict whether the patient will develop a pressure injury. For example, a computing model may be configured to generate a score indicative of the risk that the patient will develop or has an undiagnosed pressure injury. In various instances, an alert indicating the risk and/or the score can be output to a computing device associated with a care provider. Accordingly, the care provider may be notified about the patient's risk of developing the pressure injury before the pressure injury occurs, thereby enabling the care provider to take steps to prevent the pressure injury from developing.

Some examples described herein relate to systems, devices, and methods for identifying root causes of pressure injuries that have developed. For example, once a patient is diagnosed with a pressure injury, a computing model may be configured to parse through sensor data and/or EMR data to determine one or more significant risk factors associated with the patient prior to the development of the pressure injury. At least one root cause may be determined based on the risk factors experienced by the patient prior to the diagnosis of the pressure injury. In some cases, a system outputs a report summarizing the root cause(s) to a computing device associated with a care provider and/or an administrator of the care facility. Thus, the care provider and/or administrator can implement system-wide changes that can prevent patients from developing pressure injuries in the future.

Various implementations described herein can improve the technical field of patient management in a complex healthcare setting. By identifying a patient's risk of developing a pressure injury prior to the development of the pressure injury, the pressure injury can be prevented, thereby improving patient care and reducing infection risk. Furthermore, by identifying one or more root causes of a pressure injury of a patient, care providers can improve treatment of the pressure injury by addressing the root cause(s). Furthermore, care providers can improve patient management in a healthcare facility accommodating the patient by preventing the root cause(s) of the patient's pressure injury from causing other pressure injuries in other patients. In various cases, pressure injuries can be predicted, identified, and analyzed automatically based on data generated by sensors integrated with a support structure (e.g., a bed) of the patient. Furthermore, the sensor data can be integrated with the EMR data of the patient as the patient is residing on the support structure, thereby providing the opportunity for real-time analysis of a risk of the patient in developing pressure injuries, without constant supervision by a care provider.

DESCRIPTION OF THE FIGURES

The following figures, which form a part of this disclosure, are illustrative of described technology and are not meant to limit the scope of the claims in any manner.

DETAILED DESCRIPTION

Figure 1:
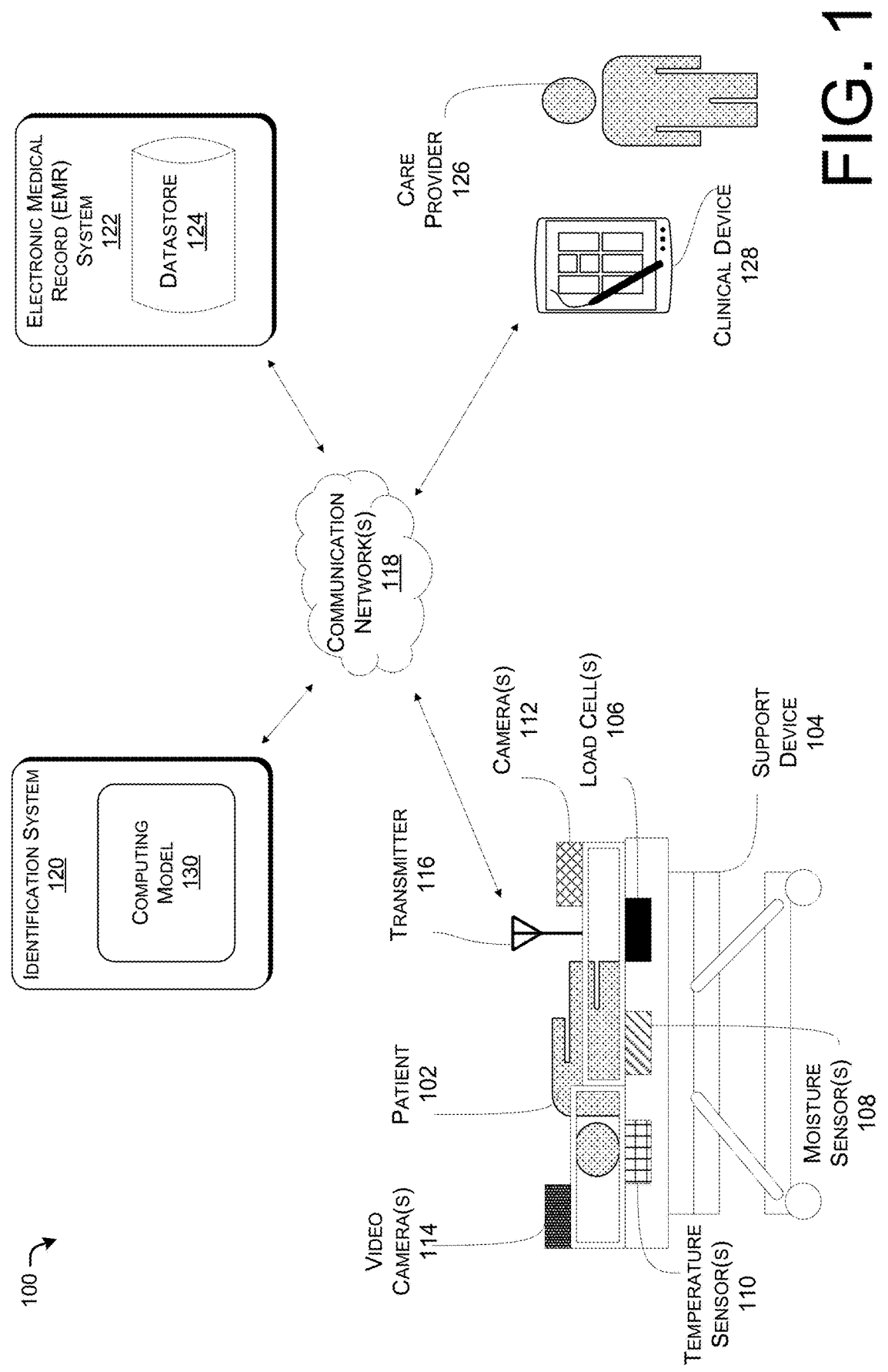
FIG. 1 illustrates an example environment for identifying pressure injuries in at least one care facility.

Various implementations of the present disclosure will be described in detail with reference to the drawings, wherein like reference numerals present like parts and assemblies throughout the several views. Additionally, any samples set forth in this specification are not intended to be limiting and merely set forth some of the many possible implementations.

FIG. 1 illustrates an example environment 100 for identifying pressure injuries in at least one care facility. As shown, a patient 102 can be associated with a support device 104. As used herein, the terms "patient," "subject," and their equivalents, can refer to a human or other animal being supported by a support device. In various cases, the patient may be admitted to a care facility, such as a hospital, hospice, clinic, urgent care facility, physician's office, or other type of clinical environment.

The support device 104 includes, for instance, a gurney, hospital bed, or some other structure configured to support the patient 102. As used herein, the terms "bed," "hospital bed," and their equivalents, can refer to a padded surface configured to support a patient for an extended period of time (e.g., hours, days, weeks, or some other time period). The patient 102 may be laying down on the support device 104. For example, the patient 102 may be resting on the support device 104 for at least one hour, at least one day, at least one week, or some other time period. In various examples, the patient 102 and the support device 104 may be located in a managed care environment, such as a hospital, or a hospice. For example, the patient 102 can be located in a medical ward of a hospital, an intensive care unit (ICU) of the hospital, or some other part of a hospital. In some implementations, the support device 104 includes a mechanical component that can change the angle at which the patient 102 is disposed. In some cases, the support device 104 includes padding to distribute the weight of the patient 102 on the support device 104. According to various implementations, the support device 104 can include vital sign monitors configured to output alarms or otherwise communicate vital signs of the patient 102 to external observers (e.g., care providers, family members, and the like). The support device 104 may include railings that prevent the patient 102 from sliding off of a resting surface of the support device 104. The railings may be adjustable, in some cases.

The support device 104 further includes various sensors. For example, the support device 104 includes one or more load cells 106. The load cell(s) 106 may be configured to detect a pressure on the support device 104. In various cases, the load cell(s) 106 can include one or more strain gauges, one or more piezoelectric load cells, a capacitive load cell, an optical load cell, any device configured to output a signal indicative of an amount of pressure applied to the device, or a combination thereof. For example, the load cell(s) 106 may detect a pressure (e.g., weight) of the patient 102 on the support device 104. In some cases, the support device 104 includes multiple load cells that respectively detect different pressures on the support device 104 in different positions along the support device 104. In some instances, the support device 104 includes four load cells arranged at four corners of a resting surface of the support device 104, which respectively measure the pressure of the patient 102 on the support device 104 at the four corners of the support device 104. The resting surface, for instance, can be a surface in which the patient 102 contacts the support device 104, such as a top surface of the support device 104.

The support device 104 may include one or moisture sensors 108. The moisture sensor(s) 108 may be configured to measure a moisture on a surface (e.g., the resting surface) of the support device 104. For example, the moisture sensor(s) 108 can include one or more capacitance sensors, one or more resistance sensors, one or more thermal conduction sensors, or a combination thereof. In some cases, the moisture sensor(s) 108 include one or more fiber sheets configured to propagate moisture to the moisture sensor(s) 108. In some cases, the moisture sensor(s) 108 can detect the presence or absence of moisture (e.g., sweat or other bodily fluids) disposed between the support device 104 and the patient 102.

In various examples, the support device 104 can include one or more temperature sensors 110. The temperature sensor(s) 110 may be configured to detect a temperature of the patient 102 and/or the support structure 104. In some cases, the temperature sensor(s) 110 includes one or more thermistors, one or more thermocouples, one or more resistance thermometers, one or more Peltier sensors, or a combination thereof.

The support device 104 may include one or more cameras 112. The camera(s) 112 may be configured to capture images of the patient 102, the support structure 104, or a combination thereof. In various cases, the camera(s) 112 may include radar sensors, infrared cameras, visible light cameras, depth-sensing cameras, or any combination thereof. In some examples, infrared images may indicate, for instance, a temperature profile of the patient 102 and/or the support structure 104. Thus, the camera(s) 112 may be a type of temperature sensor. In addition, the images may indicate a position of the patient 102 and/or the support structure 104, even in low-visible-light conditions. For example, the infrared images may capture a position of the patient 102 during a night environment without ambient lighting in the vicinity of the patient 102 and/or the support structure 104. In some cases, the camera(s) 112 may include one or more infrared video cameras. The camera(s) 112 may include at least one depth-sensing camera configured to generate a volumetric image of the patient 102, the support structure 104, and the ambient environment. According to various implementations, the images and/or videos captured by the camera(s) 112 are indicative of a position and/or a movement of the patient 102 over time.

According to some examples, the support device 104 can include one or more video cameras 114. The video camera(s) 114 may be configured to capture videos of the patient 102, the support structure 104, an entrance to a room containing the support structure 104, an entrance to a bathroom adjacent to the room containing the support structure 104, or a combination thereof. The videos may include multiple images of the patient 102 and/or the support structure 104. Thus, the videos captured by the video camera(s) 114 may be indicative of a position and/or movement of the patient 102 over time. In some examples, the video camera(s) 114 capture visible light videos, changes in radar signals over time, infrared videos, or any combination thereof.

In some examples, the support structure 104 includes a head rail and a foot rail. The camera(s) 112 and/or video camera(s) 114, for instance, are mounted on the head rail, the foot rail, an extension (e.g., a metal structure) attached to the head rail or the foot rail, or any combination thereof. In various implementations, the camera(s) 112 and/or video camera(s) 114 are attached to a wall of the room containing the support structure 104. In some examples, the camera(s) 112 and/or video camera(s) 114 are attached to a cart (e.g., a support structure on wheels) that is located in the vicinity of the support structure 104.

In various cases, the sensors (e.g., the load cell(s) 106, the moisture sensor(s) 108, the temperature sensor(s) 110, the camera(s) 112, the video camera(s) 114, or any combination thereof) of the support device 104 are configured to monitor one or more parameters of the patient 102 and to generate sensor data associated with the patient 102. In various cases, the sensors convert analog signals (e.g., pressure, moisture, temperature, light, electric signals, or any combination thereof) into digital data that is indicative of one or more parameters of the patient 102. As used herein, the terms "parameter," "patient parameter," and their equivalents, can refer to a condition of an individual and/or the surrounding environment. In this disclosure, a parameter of the patient 102 can refer to a position of the patient 102, a movement of the patient 102 over time (e.g., mobilization of the patient 102 on and off of the support device 104), a pressure between the patient 102 and an external object (e.g., the support device 104), a moisture level between the patient 102 and the support device 104, a temperature of the patient 102, a vital sign of the patient 102 (e.g., a blood pressure, a peripheral oxygenation level, a heart rate, a respiration, a blood volume, or some other vital sign), a nutrition level of the patient 102, a medication administered and/or prescribed to the patient 102 (e.g., a vasopressor or any other medication that impacts pressure injury risk), a previous condition of the patient 102 (e.g., the patient was monitored in an ICU, in dialysis, presented in an emergency department waiting room, etc.), a skin tone of the patient 102 (e.g., which may impact whether care providers readily identify pressure injuries on the skin of the patient 102), circulation of the patient 102 (e.g., restricted blood flow), a pain level of the patient 102, the presence of implantable or semi-implantable devices (e.g., ports, tubes, catheters, other devices, etc.) in contact with the patient 102, or any combination thereof. Optionally, a parameter is specific to a limb, such as an arm or a leg of the patient 102. In various examples, the support device 104 generates data indicative of one or more parameters of the patient 102 using the load cell(s) 106, the moisture sensor(s) 108, the temperature sensor(s) 110, the cameras 112, the video camera(s) 114, or a combination thereof. The data generated by the support device 104 be referred to herein as "sensor data."

The support device 104 may further include a transmitter 116. The transmitter 116 may be configured to transmit the sensor data from the support device 104 over one or more communication networks 118. The communication network(s) 118 may include one or more wired networks (e.g., at least one wired local area network (LAN), at least one fiber-optic network, or some other type of wired network), one or more wireless networks (e.g., at least one wireless LAN, at least one WI-FI network, at least one BLUETOOTH network, at least one cellular network, or some other type of wireless network), or a combination thereof. In some cases, the communication network(s) 118 include one or more wide area networks (WANs), such as the Internet. In some cases, the transmitter 116 includes a transceiver configured to receive signals from the communication network(s) 118.

In some examples, the sensors (e.g., the load cell(s) 106, the moisture sensor(s) 108, the temperature sensor(s) 110, the camera(s) 112, the video camera(s) 114, or any combination thereof) can include contact-free continuous monitoring (CFCM) sensors. For instance, a sensing pad including the sensors integrated or otherwise attached to a support substrate (e.g., a flexible substrate) can be placed above or below a mattress of the support device 104. Accordingly, the patient 102 may move freely without being encumbered by the presence of the sensors. In some cases, the sensing pad is removable from the support device 104. The sensing pad, in some cases, includes the transmitter 116. For instance, the sensing pad may include transmitter(s) that transmit data over the communication network(s) 118.

According to various implementations described herein, the support device 104 may transmit the sensor data to an identification system 120 over the communication network(s) 118. The identification system 120 may be configured to transmit and/or receive data over the communication network(s) 118. The identification system 120 may be embodied in hardware, software, or a combination thereof. In some cases, the identification system 120 is hosted on one or more computing devices located in a local environment of the support device 104. For example, the identification system 120 may be hosted on an on-premises server located in a hospital in which the support device 104 is also located. In some cases, the identification system 120 is hosted by one or more computing devices located remotely from the premises of the support device 104. For example, the identification system 120 may be hosted in a distributed computing environment, such as a cloud computing environment.

The environment 100 may also include an electronic medical record (EMR) system 122. The EMR system 122 may be configured to transmit and/or receive data over the communication network(s) 118. The EMR system 122 may be embodied in hardware, software, or a combination thereof. In some examples, the EMR system 122 is hosted on one or more computing devices located in a local environment of the support device 104. For example, the EMR system 122 may be located on an on-premises server located in a hospital in which the support device 104 is also located. In some cases, the EMR system 122 is hosted by one or more computing devices located remotely from the premises of the support device 104. For example, the EMR system 122 may be hosted in a distributed computing environment, such as a cloud computing environment. In some cases, the EMR system 122 and the identification system 120 are hosted by the same computing device(s).

The EMR system 122 may be configured to store and/or manage medical records associated with a population of patients that include the patient 102. The EMR system 122 may include a datastore 124 that stores the medical records of the patients. The datastore 124, for instance, can include one or more databases. As used herein, the terms "electronic medical record," "EMR," "electronic health record," "EHR," and their equivalents, can refer to a collection of digital data indicative of the medical status and/or medical history of an individual patient. An EMR of the patient 102, for instance, can indicate the immunization record of the patient 102, diagnostic images taken of the patient 102, a list of medications of the patient 102, a list of allergies of the patient 102, demographics of the patient 102, laboratory tests of the patient 102, previous visits of the patient 102 to a healthcare setting (e.g., a hospital, a clinic, or another type of healthcare setting), procedures performed on the patient 102, a medical history of the patient 102 (e.g., whether the patient 102 was previously on dialysis, using a feeding tube, in the emergency department, etc.), and so on. The EMR system 122 can therefore store any of the types of parameters that are discussed herein.

In various cases, the EMRs managed by the EMR system 122 can be generated and/or modified by medical personnel, such as a care provider 126. The care provider 126, for instance, may be associated with a clinical device 128. The clinical device 128 may include a computing device, such as a desktop computer, a laptop computer, a tablet computer, a smartphone, or any other type of user equipment (UE). In various examples, the care provider 126 can generate and/or modify (e.g., update) the EMRs of various patients (including the patient 102) that are stored by the EMR system 122. For example, the care provider 126 may measure a vital sign (e.g., a blood pressure) of the patient 102. The care provider 126, via a web browser of the clinical device 128 and/or an application of the clinical device 128, may enter the vital sign. The clinical device 128 may transmit, to the EMR system 122 over the communication network(s) 118, data indicating the vital sign. In response to receiving the data, the EMR system 122 may update the EMR of the patient 102 to indicate the measured vital sign.

According to some examples, the care provider 126 can enter notes into the EMRs. As used herein, the term "note," and is equivalents, can refer to text indicative of observations and/or care provided to a patient by a care provider. For example, the care provider 126 may observe the patient 102 and may enter, using the clinical device 128, a note explaining a condition of the patient 102, tests performed by the patient 102, ongoing monitoring performed on the patient 102, procedures performed on the patient 102, diagnoses of the patient 102, symptoms of the patient 102, and the like. Notes associated with the patient 102 may be stored, by the datastore 124, in the EMR of the patient 102.

In some cases, the identification system 120 and/or the EMR system 122 may be configured to perform natural language processing on notes stored in the datastore 124. For example, the identification system 120 and/or the EMR system 122 may be configured to analyze a note in the EMR of the patient 102 to recognize words and/or phrases associated with a sensory response of the patient 120 (e.g., "sensitivity," "responsiveness," "sensitive to touch," etc.). The EMR data may encompass recognized words in notes of the EMRs stored in the datastore 124.

In various examples, the EMRs managed by the EMR system 122 can be viewed and/or modified by various devices, such as the clinical device 128. In some cases, the EMRs can be accessed by devices in different locations, hospital systems, insurance companies, care facilities, or other types of environments.

In some implementations, the identification system 120 is configured to generate, manage, and/or adjust a computing model 130 based on the sensor data and/or the EMRs stored by the EMR system 122. In various cases, the computing model 130 is configured to identify a risk that the patient 102 will or has developed a pressure injury based on the sensor data from the support device 104 and/or the EMR of the patient 102 stored in the datastore 124 of the EMR system 122.

As used herein, the term "pressure injury," and its equivalents, can refer to any injury caused due to pressure and/or friction between the skin of a patient and the surface of an object. Pressure sores and pressure ulcers are examples of pressure injuries. Pressure injuries can be defined by stages. A Stage 1 pressure injury can refer to an area of skin that is warmer than surrounding tissue, firmer or softer than surrounding tissue, reddened, resistant to blanching, painful, but may not be an open wound. A Stage 2 pressure injury can refer to an opening or fluid-filled blister in skin (e.g., an ulcer) that is tender and painful. A Stage 3 pressure injury can refer to a sore that extends into tissue below the skin, such that fat may be visible within the sore. A Stage 4 pressure injury can refer to a wound that reaches from the skin into muscle and/or bone and can cause extensive damage to the patient.

Various factors affect a risk of developing a pressure injury. The Braden Scale, for example, utilizes factors such as sensory perception, moisture, activity, mobility, nutrition, friction, and shear to estimate a patient's risk of developing a pressure ulcer. Temperature may also impact a risk of developing a pressure injury and/or may be indicative of a pressure injury that has already developed. The sensor data from the support device 104 and/or the EMR from the EMR system 122 can correspond to factors that impact the risk that the patient 102 has or will develop a pressure injury. For example, the sensor data generated by the moisture sensor(s) 108 may correspond to an exposure of the patient 102 to moisture; the sensor data generated by the load cell(s) 106, camera(s) 112, and video camera(s) 116 can correspond to an activity, mobility, friction, and/or shear of the patient 102 with respect to the support device 104 and/or another type of object (e.g., an implantable device, a semi-implantable device, etc.); the EMR of the patient 102 may include data corresponding to the nutrition of the patient 102; and the sensor data generated by the temperature sensor(s) 110 and/or camera(s) 112 can correspond to the temperature of the patient 102. In some cases, the sensory perception of the patient 102 can be identified based on notes stored in the EMR of the patient 102. For example, the care provider 126 may assess the sensory perception of the patient 102 and record one or more assessments of the sensory perception of the patient 102 in the EMR of the patient 102.

According to some implementations, the computing system 120, when executing the computing model 130, calculates a score indicating a risk of the patient 102 for developing and/or having a pressure injury. As used herein, the terms "aggregate score," "score," and their equivalents, can refer to at least one numerical indicator. For example, the computing model 130 may include the following Formula 1 to generate the score:

$$S = f_m(s_m) + f_a(s_l, s_{ir}, s_c) + f_n(r_n) + f_i(s_{ir}, s_t) + f_s(r_s) \qquad \text{Equation 1}$$

wherein S is the score indicative of the risk of the patient 102 for having and/or developing a pressure injury, $f_m(\ )$ is a function for calculating the factor of moisture in the risk, $s_m$ is sensor data from the moisture sensor(s) 108, $f_a(\ )$ is a function for calculating the factor of activity, mobility, friction, and/or shear in the risk, $s_l$ is the sensor data from the load cell(s) 106, $s_{ir}$ is the sensor data from the camera(s) 112, $s_c$ is the sensor data from the video camera(s) 116, $f_n(\ )$ is a function for calculating the factor of nutrition in the risk, $r_n$ is a nutrition record of the patient 102 stored in the EMR of the patient 102, $f_i(\ )$ is a function for calculating the factor of temperature in the risk, $s_t$ is the sensor data from the temperature sensor(s) 110, $f_s(\ )$ is a function for calculating the factor of sensory perception in the risk, and $r_s$ is a sensory perception record of the patient 102 stored n the EMR of the patient 102. In some cases, one or more of $f_m(\ )$, $f_a(\ )$, $f_n(\ )$, $f_i(\ )$, or $f_s(\ )$ can be omitted from Equation 1. In some examples, the computing model 130 may generate a Braden Score of the patient 102 based on the sensor data from the support device 104 and/or the EMR of the patient 102 stored in the datastore 124 of the EMR system 122.

According to some examples, the computing model 130 can be a machine learning model and can be trained to identify the risk based on training data. As used herein, the term "machine learning model," and its equivalents, can refer to a computer-based model configured to identify patterns in data, and which can improve its pattern recognition based on training data. For example, the computing model 130 can include at least one of a deep learning model, a linear regression model, a logistic regression model, a gradient boost machine, or some other machine learning model. In various cases, the training data can include sensor data from multiple support devices (including or excluding the support device 104) and EMR data from multiple EMRs, which may be associated with multiple patients (including or excluding the patient 102). The training data may also indicate whether those patients developed pressure injuries, the severity of the pressure injuries, and the like. Using the training data, one or more numerical factors of the computing model 130 can be optimized to accurately predict the risk of pressure injuries based on sensor data and EMR data. This process of optimization can be referred to as "training." Once trained, the computing model 130 can be configured to accurately output the risk of the patient 102 for developing and/or having a pressure injury based on inputs including one or more parameters of the patient 102, which may be indicated by the sensor data from the support device 104 and/or the EMR of the patient 102 from the EMR system 122.

In some cases, the identification system 120 is configured to determine whether the patient 102 is at risk for a pressure injury based on the sensor data. For example, the sensor data from the support device 104 and or the EMR of the patient 102 may be input into the (e.g., pre-trained) computing model 130, such that the identification system 120 can determine the risk of the patient 102 for developing and/or having the pressure injury using the computing model 130. In some cases, the identification system 120 may store the risk locally and/or in the EMR of the patient 102, such that the care provider 126 can access the risk on-demand using the clinical device 128.

In some implementations, the identification system 120 can selectively generate an alert based on the risk. The identification system 120 may compare the risk to a threshold. Based on the comparison, the identification system 120 may generate and/or output an alert to the EMR system 122 and/or the clinical device 128. The alert may indicate that the patient 102 is at a relatively high risk for developing and/or having a pressure injury. In some cases, the identification system 120 may identify, based on the sensor data, a location of the potential and/or suspected pressure injury on the skin of the patient 102. In some examples, the alert may further indicate one or more potential causes of the pressure injury. For example, the identification system 120 may compare $f_m$( ), $f_a$( ), $f_n$( ), $f_t$( ), or $f_s$( ) to a threshold, and report moisture, activity, nutrition, temperature, or sensory perception as a potential cause of the pressure injury based on the comparison. In some cases, the alert may be output by the clinical device 128 to the care provider 126, causing the care provider 126 to provide assistance to the patient 102, thereby preventing the pressure injury or preventing the pressure injury from getting worse.

In particular examples, the score representing the risk is proportional to the risk of the patient 102 to having and/or developing a pressure injury. For instance, the score may be in a range from 0 to 100, wherein a score of 0 represents a certainty that the patient 102 is not developing a pressure injury and a score of 100 represents a certainty that the patient 102 has a pressure injury. The threshold may be 50. If the patient 102 has a score that is greater than 50, then the identification system 120 may generate an alert indicating that the patient 102 is in danger of developing a pressure injury and may transmit the alert to the clinical device 128. If the contribution of moisture to the score is greater than a threshold (i.e., if $f_m$( ) exceeds another threshold), then the alert may be generated to indicate that moisture is a significant factor in risk of the patient 102 for developing a pressure injury. If the patient 102 has a score that is less than or equal to 50, then the identification system 120 may refrain from generating and/or transmitting the alert. In some cases, the score may exceed the threshold before the patient 102 actually develops the pressure injury. Accordingly, in some examples described herein, the pressure injury of the patient 102 can be prevented by the care provider 126.

According to some implementations, the alert indicates one or more recommended interventions to treat and/or prevent a pressure injury of the patient 102. The recommended interventions include, for instance, an instruction for safe handling of the patient 102, providing an improved surface (e.g., placing a cushion, tape, or the like between an object, such as the support device 104, an implantable device, or a semi-implantable device, and the patient 104), consulting an expert (e.g., a WOCN), scheduling a consultation (e.g., in-person or virtual via the computing device 128) with the expert, turning the patient 102, adding or replacing pads (e.g., incontinence pads disposed on the support structure 104), mobilizing the patient 102, adjusting nutrition of the patient 102, modifying an incontinence pad changing schedule, or a combination thereof. In some cases, the alert includes recommended interventions that are based on one or more parameters of patient 102. For example, if the risk of the patient 102 for developing a pressure injury based on moisture is above a threshold, then the identification system 120 generates the alert to specifically include recommended interventions specific to addressing moisture (e.g., adding or replacing pads, modifying an incontinence pad changing schedule, etc.).

In some examples, the score is generated with respect to a particular body part of the patient 102 (e.g., a limb of the patient 102), and the alert indicates that the particular body part of the patient 102 has or is in danger of developing a pressure injury. For instance, the score can be generated based on a parameter detected by an infrared or heat sensor monitoring an arm of the patient 102, and the alert may specifically indicate that the arm of the patient 102 is in danger of developing a pressure injury. In some cases, the score can be generated based on a procedure (e.g., intubation, ostomy, etc.) performed on the body part of the patient 102 and the alert can identify the body part impacted by the procedure. In some cases, the recommended interventions included in the alert are specific to addressing the risk of pressure injury of the body part.

In some implementations, the score is generated with respect to a group of patients including the patient 102. For example, the identification system 120 generates scores indicating the risk that each patient in the group has and/or will develop a pressure injury and aggregates the scores. The aggregated score may indicate the risk that the group, as a whole, have and/or will develop pressure injuries. In some cases, the identification 120 can generate the score based on a history of wounds within the group, a type of unit (e.g., ICU, in-patient ward, a floor of a hospital, etc.) that the group is associated with, staffing of the unit, whether the unit is accepting overflow from other units, seasonal trends associated with the unit, a number of pressure injury cases that have been diagnosed within the unit in a particular time period (e.g., the previous day, week, etc.), or a combination thereof. The identification system 120 can identify recommended interventions including adding additional staff to the unit, adding specialized staff (e.g., WOCNs) to the unit, ordering and/or delivering specialized equipment to the unit that can prevent wounds (e.g., lifts, walkers, specialized versions of the support device 104, etc.), or a combination thereof.

In various implementations described herein, the identification system 120 can identify that the patient 102 has a pressure injury and use the sensor data from the support device 104 and/or the EMR of the patient 102 to identify one or more root causes of the pressure injury. As used herein, the term "root cause," and its equivalents, can refer to a risk factor that is likely to have caused a known pressure injury.

According to some examples, the identification system 120 may identify that the patient 102 has a pressure injury based on the EMR of the patient 102 and/or a message from the clinical device 128. For example, the care provider 126 may observe a pressure injury on the patient 102 and may generate a note indicating the pressure injury in the EMR of the patient 102 that is stored in the datastore 124 of the EMR system 122. The identification system 120 and/or the EMR system 122 may perform natural language processing on the note in order to enable the identification system 120 to identify the pressure injury.

Once the pressure injury of the patient 102 is identified, the identification system 120 can identify one or more root causes of the pressure injury. The identification system 120 may identify sensor data from the support device 104 obtained prior to the identification of the pressure injury (e.g., by the care provider 126 and/or the identification system 120). In addition, the identification system 120 may access EMR data corresponding to the condition of the patient 102 and/or care performed on the patient 102 prior to the identification of the pressure injury. The identification system 120 may perform a post-hoc analysis on the sensor data and/or the EMR data to identify the one or more root causes of the pressure injury. In some cases, the identification system 120 can calculate a contribution of a potential root cause to the pressure injury risk of the patient 102. Potential root causes can include, for example, the presence of moisture in contact with the patient 102, an amount of moisture in contact with the patient 102, an amount of time that moisture was in contact with the patient 102, an amount of pressure between the patient 102 and the support device 104, an amount of time that greater than a threshold pressure was between the patient 102 and the support device 104 without interruptions, an amount of time that the patient 102 rested on the support device 104 without moving, an amount of time that the patient 102 rested on the support device without getting up from the support device 104, an amount of pressure between the patient 102 and the support device 104 during movement of the patient 102, an amount of rubbing between the patient 102 and the support device 104, a temperature of the patient 102 (e.g., at a point of contact between the patient 102 and the support device 104), a nutrition level of the patient 102, a sensitivity of the patient 102 to physical examination, a presence and/or duration of implantable or semi-implantable devices in contact with the patient 102, a duration of a surgical procedure performed on the patient 102, an amount of time that the patient 102 was in a particular position (e.g., an incline position) during a procedure, and the like. Semi-implantable devices include, for instance, catheters placed in the patient 102, drains placed in the patient 102, and tubes (e.g., ventilation tubes) placed in the patient 102. Implantable and semi-implantable devices are example sources of pressure injuries. In some cases, potential root causes can be identified by the computing model 130 using machine learning. For example, the computing model 130 may be trained to optimize correlations between the potential root causes and risks of pressure injuries based on training data that includes sensor data and/or EMR data from other patients who have experienced pressure injuries.

According to some examples, the computing model 130 includes a component model for each potential root cause. By inputting at least a component of the sensor data and/or the EMR data into a component model, the component model may output a statistic that corresponds to the estimated contribution of the associated potential root cause on the pressure injury. For example, a component model associated the potential root cause of "an amount of pressure between the patient 102 and the support device 104 during movement of the patient 102" may be in put with data obtained by the load cell(s) 106 (indicating the amount of pressure), data obtained by the camera(s) 112 (indicating the movement), and data obtained by the video camera(s) 116 (indicating the movement). In some cases, the statistic for each root cause may be between 0 and 100, wherein 0 represents a certainty that the potential root cause did not contribute to the pressure injury and 100 represents a certainty that the potential root cause did cause the pressure injury. According to some examples, each potential root cause whose output from its associated component model exceeds a threshold (e.g., 50) may be determined to be an actual root cause of the pressure injury. In some cases, one or more of the potential root causes whose component models output the highest statistics may be determined to be root cause(s) of the pressure injury. For example, the three highest statistics of the total group of root causes may be determined to be the three root causes of the pressure injury.

In various cases, the identification system 120 may generate a report indicating the root cause(s) of the pressure injury of the patient 102. The report may be transmitted to the clinical device 128 or to some other computing device, such as a computing device associated with a family member of the patient 102. The clinical device 128 may output the report to the care provider 126, thereby providing the care provider 126 with context about the pressure injury. According to some examples, the other computing device may output the report to user (e.g., the family member), and prompt the user for confirmation of the pressure injury. In some examples, the clinical device 128 and/or other computing device may prompt a user to input a picture of the skin of the patient 102 at the location of the suspected pressure injury. In some cases, the identification system 120 may transmit the report to the EMR system 122, which may store the report in the EMR of the patient 102.

Although not illustrated in FIG. 1, in some cases, the identification system 120 can utilize data from multiple support devices in order to identify risks of various patients resting on the multiple support devices. In some examples, the identification system 120 can output alerts and/or reports to multiple clinical devices associated with multiple care providers. In some cases, the identification system 120 can generate a single report indicating one or more common root causes of pressure injuries of a group of patients whose care was managed by a single care facility (e.g., a hospital). The report could be output to a device associated with an administrator of the facility. Thus, the administrator can implement changes to policies within the care facility to address common sources of pressure injuries, thereby preventing future pressure injuries in patients managed by the care facility.

Figure 2:
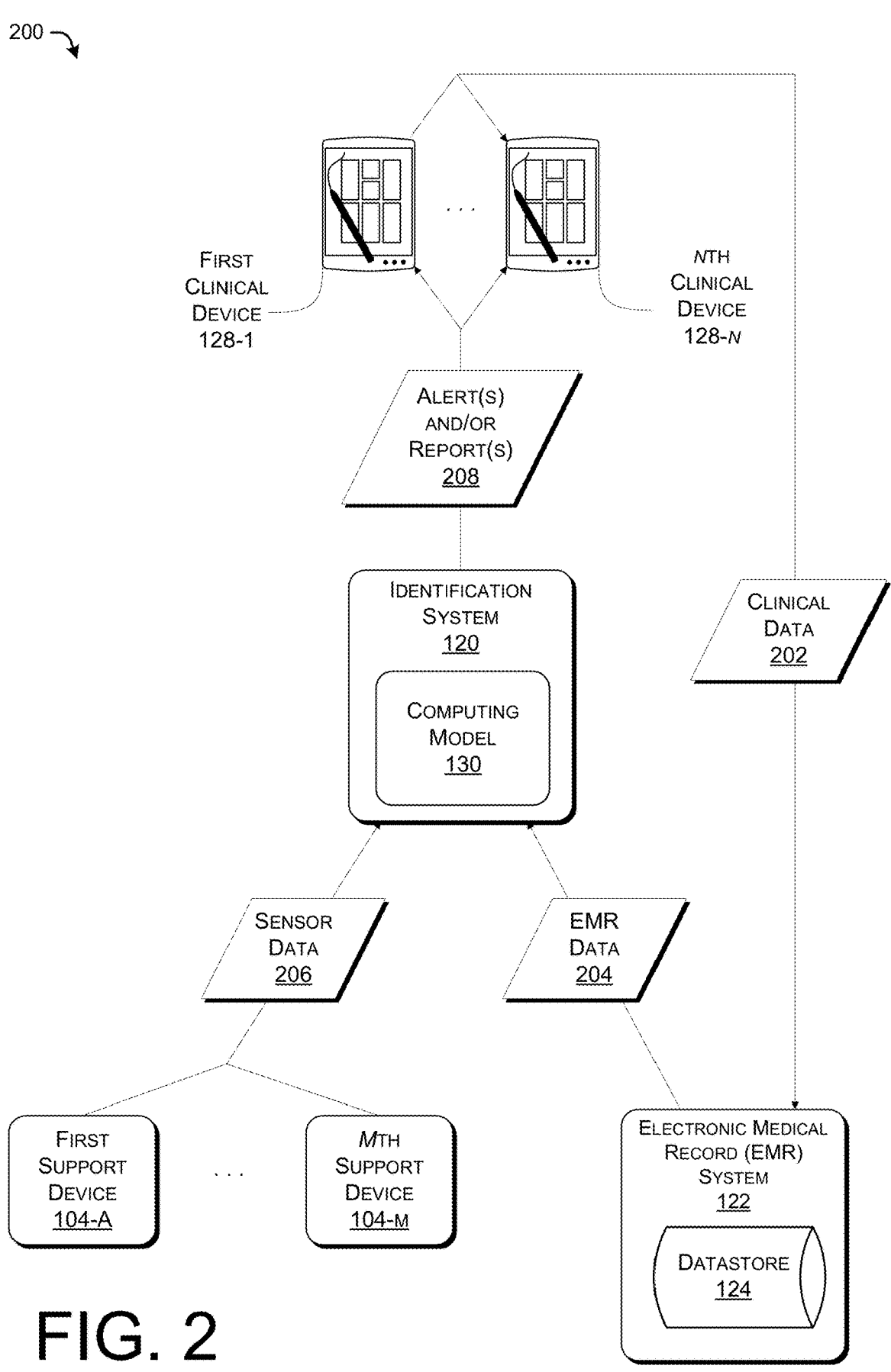
FIG. 2 illustrates example signaling for identifying, predicting, and analyzing pressure injuries in a clinical environment.

FIG. 2 illustrates example signaling 200 for identifying, predicting, and analyzing pressure injuries in a clinical environment. As shown, the signaling 200 involves the identification system 120, the EMR system 122, the datastore 124, and the computing model 130 described above with reference to FIG. 1. Further, the signaling involves first to nth clinical devices 128-1 to 128-n, which may include the clinical device 128 described above with reference to FIG. 1. The signaling 200 may also involve first to mth support devices 104-1 to 104-m, which may include the support device 104 described above with reference to FIG. 1. The values of n and m may each be positive integers.

In various examples, the first to nth clinical devices 128-1 to 128-n may be operated by various users within the clinical environment. For example, the clinical devices 128-1 to 128-n may be carried, operated, viewed, or otherwise utilized by care providers, such as physicians, physician assistants, nurses, medical technicians, and the like. In some examples, the first to nth clinical devices 128-1 to 128-n include one or more UEs, mobile phones, tablet computers, laptop computers, desktop computers, servers, or other types of computing devices. In some cases, the first to nth clinical devices 128-1 to 128-n include at least one display that can output alerts to a team of care providers. For instance, the first to nth clinical devices 128-1 to 128-n may include one screen simultaneously displaying the statuses of multiple patients at a nurse station, doctor's lounge, or other shared space in the clinical environment. In some cases, the first to nth clinical devices 128-1 to 128-n may include one or more medical devices, such as magnetic resonance imaging (MRI) scanners, surgical robots, vital sign monitors, or other types of medical devices.

In various examples, the first to nth clinical devices 128-1 to 128-n transmit clinical data 202 to the EMR system 122. The clinical data 202 can include any data indicative of a status or a condition of a patient in the clinical environment. For example, the clinical data 202 can include patient information (e.g., demographics, identity, age, etc.), medical histories (e.g., previous surgical procedures, treatments, conditions, etc.), test results (e.g., electrolyte levels, vital sign measurements, etc.), imaging (e.g., x-ray images, ultrasound images, etc.), care plans, notes, and the like. In some cases, the first to nth clinical devices 128-1 to 128-n execute an applications and/or browsers that provide user interfaces (UIs) for various care providers. The clinical data 202 can be generated by the first to nth clinical devices 128-1 to 128-n based on user inputs to the first to nth clinical devices 128-1 to 128-n. The user inputs can be input through various user input devices, such as keyboards, touchscreens, at the like.

The EMR system 122 may sort the clinical data 202 based on patient and store the sorted clinical data 202 in respective EMRs of the patients. The EMRs may be stored in the datastore 124. In some cases, the clinical data 202 includes multiple data flows and/or packets that are tagged according to patient. For example, a patient may be associated with a unique identifier (e.g., a string, a number, a code, or another type of indicator) that is included in each data packet carrying medical information of the patient. Thus, the EMR system 122 may store various portions of the clinical data 202 by patient in appropriate EMRs.

According to some implementations, the EMR system 122 may extract portions of the clinical data 202 and return the clinical data 202 to the first to nth clinical devices 128-1 to 128-n. For example, any of the first to nth clinical devices 128-1 to 128-n may receive an input requesting at least a portion of an EMR of a particular patient, and a corresponding request can be transmitted to the EMR system 122. The EMR system 122 may transmit the clinical data 202 to the requesting one of the first to nth clinical devices 128-1 to 128-n, thereby enabling care providers to view EMRs of their patients.

In some cases, the EMR system 122 may transmit EMR data 204 to the identification system 120. The EMR data 204 may include a least a portion of the data stored in the EMRs of the datastore 124. For example, the EMR data 204 includes at least some of the clinical data 202. In some cases, the EMR data 204 includes data related to risks of the patients associated with having and/or developing pressure injuries. In some cases, the EMR data 204 includes notes written by the care providers. According to some implementations, the EMR system 122 may perform natural language processing on the notes in the clinical data 202, identify words indicative of pressure injuries and/or causes of pressure injuries in the notes, and may include indications of those words in the EMR data 204. In some examples, the EMIR data 204 indicates patients diagnosed with pressure injuries, physical therapies performed on the patients that may prevent pressure injuries, nutrition levels of the patients, sensory perception reports of the patients, and the like. Nutrition levels, for instance, can include levels (e.g., concentrations) of molecules measured in blood, serum, or other bodily fluids (e.g., serum albumin, prealbumin, transferrin, retinal-binding protein, etc.); levels of molecules in food and/or fluids administered to the patients (e.g., calories, protein levels, zinc, Vitamin A, Vitamin C, Vitamin D, arginine, glutamine, etc.); and/or other characteristics of the patients related to nutrition (e.g., hydration levels of the patient, weight changes of the patient, etc.).

In addition, the first to mth support devices 104-1 to 104-m may transmit sensor data 206 to the identification system 120. The first to mth support devices 104-1 to 104-m may be hospital beds that include sensors. For example, the first to mth support devices 104-1 to 104-m may include one or more load cells, one or more moisture sensors, one or more temperature sensors, one or more infrared cameras, one or more video cameras, or any combination thereof. The sensor data 206 may be generated based on measurements by the sensors of the first to mth support devices 104-1 to 104-m. The various parameters detected by the sensors may be indicative of pressure injury risks of the patients supported by the first to mth support devices 104-1 to 104-m. In various cases, the EMR data 204 and the sensor data 206 may correspond to the same patients.

In various cases, the identification system 120 may train the computing model 130 based on the EMR data 204 and/or the sensor data 206. For example, the identification system 120 may optimize one or more factors of the computing model 130 to enable the computing model 130 to accurately predict a risk of a patient in developing a pressure injury based on the EMR data 204 and/or the sensor data 206 of the patient. Accordingly, the identification system 120 may be optimized to correlate the EMR data 204 and the sensor data 206 to risks of patients of developing pressure injuries.

The identification system 120 may use the trained computing model 130 to predict patients that are developing pressure injuries. For example, if a patient has more than a threshold risk of developing a pressure injury, the identification system 120 may generate an alert indicating that the patient is at risk of developing a pressure injury.

According to various implementations, the identification system 120 may identify root causes of pressure injuries of the patients based on the EMR data 204 and/or the sensor data 206. For example, upon identifying that one of the patients has been diagnosed with a pressure injury (e.g., based on the EMR data 204), the identification system 120 may identify one or more root causes of the pressure injury based on the EMR data 204 and/or the sensor data 206. The identification system 120 may generate a report indicating the root cause(s) of the pressure injury. In some cases, the identification system 120 may generate the report to indicate root causes of multiple pressure injuries in the clinical environment, which may be conducive for identifying general trends for improving care within the clinical environment.

The identification system 120 may output the alert(s) and/or report(s) 208 to one or more of the first to nth clinical devices 128-1 to 128-*n*. The alert(s) and/or report(s) 208 can be output by the first to nth clinical devices 128-1 to 128-*n*. Thus, care providers may be notified of patients at risk of developing pressure injuries and/or potential deficiencies in care that have led to patients developing pressure injuries.

Although not specifically illustrated in FIG. 2, the clinical data 202, the EMR data 204, the sensor data 206, the alert(s) and/or report(s) 208, or any combination thereof, may be transmitted as data packets over one or more communication networks, such as the communication network(s) 118 described above with reference to FIG. 1. Furthermore, the clinical data 202, the EMR data 204, the sensor data 206, the alert(s) and/or report(s) 208, or any combination thereof may be encrypted and/or transmitted over virtual private networks (VPNs) to maintain confidentiality of sensitive patient-related medical information.

Figure 3:
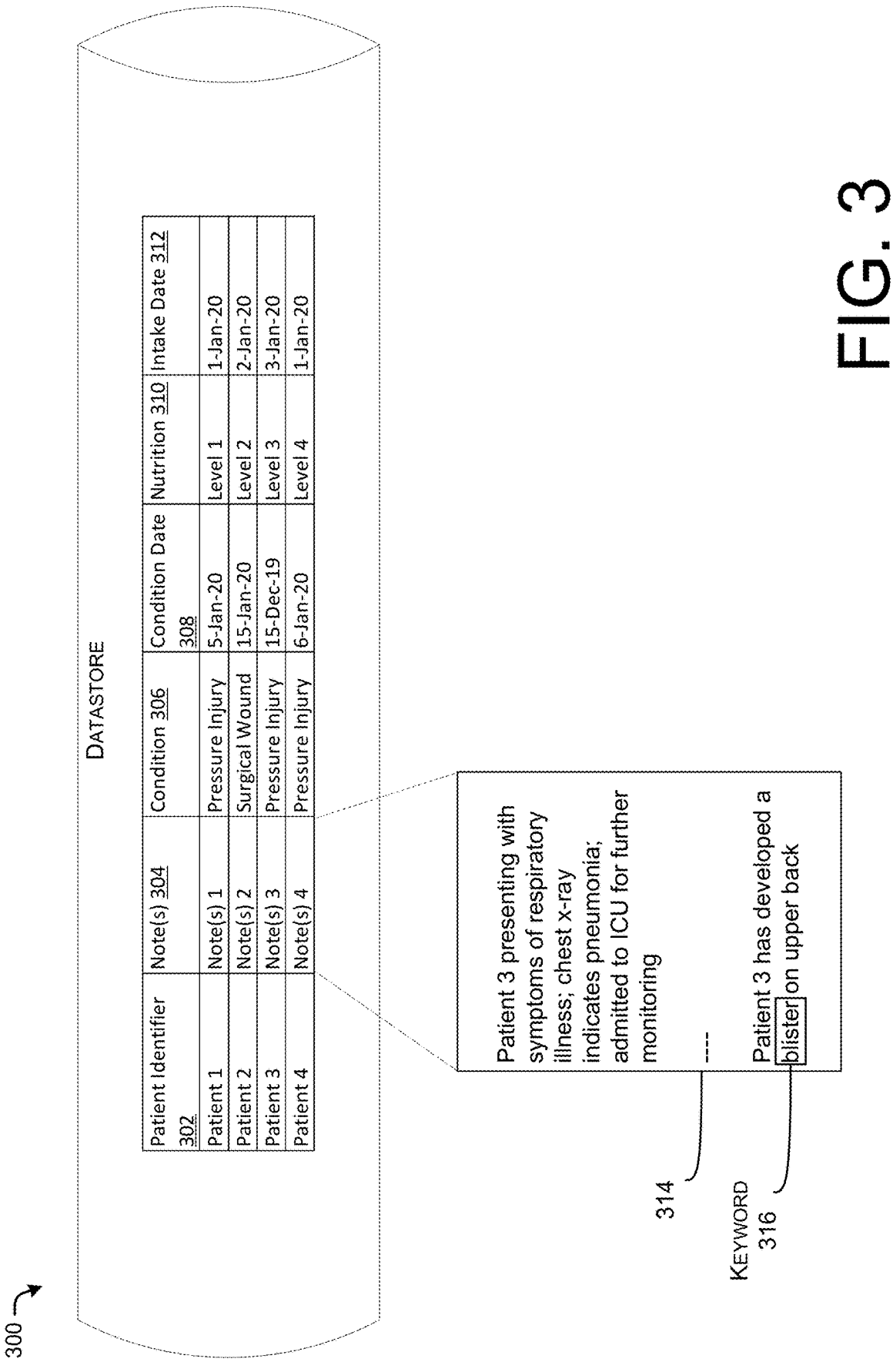
FIG. 3 illustrates an example of a datastore storing EMRs of patients in a clinical environment.

FIG. 3 illustrates an example of the datastore 124 described above with reference to FIGS. 1 and 2. The datastore 124 stores EMRs of various patients in a table 300. In the example illustrated in FIG. 3, EMRs of four different patients are pictured, but implementations are not so limited. In some cases, the datastore 124 stores EMRs of hundreds, thousands, or even millions of patients.

The table 300 includes multiple data fields, such as a patient identifier 302 field, a note(s) 304 field, a condition 306 field, a condition date 308 field, a nutrition 310 field, and an intake data 312 field. In various implementations, the table 300 can store numerous other data fields than the ones illustrated in FIG. 3. As shown in FIG. 3, the data fields are arranged in columns and the EMRs of the four patients are arranged in rows. The patient identifier 302 field may store a unique identifier for each of the four patients. The note(s) 304 field may store one or more notes associated with conditions of each patient. The note(s) 304 may be entered into each EMIR by care providers and may include text that reflects examinations, diagnoses, status, conditions, or any other clinically relevant information, of the patients. The condition 306 field may store one or more medical conditions of each patient. The condition date 308 field may indicate a date on which the condition(s) for each patient are diagnosed. The nutrition 310 field may indicate a nutrition level of each patient. The intake date 312 field may indicate the date at which a care facility began caring for each patient.

In various cases, the note(s) 304 of each EMR may include text. For example, sample Note(s) 4 314 includes text associated with at least one of an examination, a diagnosis, a condition, a status, or other clinically relevant information, of Patient 4. To identify whether any of the note(s) 304 indicate a pressure injury and/or a condition associated with a risk of developing a pressure injury, natural language processing may be performed on the note(s) 304. One or more keywords associated with pressure injuries and/or risks of developing a pressure injury may be identified within the note(s) 304. Keywords associated with pressure injuries can include, for instance, "wound," "ulcer," "blister," "sore," "pressure injury," "ulcer," "pressure ulcer," "hospital acquired pressure injury," "HAPI," their equivalents, or any combination thereof. Keywords associated with risks of developing pressure injuries can include, for instance, "reduced mobility," "prone," "reduced sensory perception," "poor circulation," or any combination thereof.

For example, Note(s) 4 314 may include a first note and a second note, wherein the second note includes a keyword 316 associated with a pressure injury. The keyword 316, for instance, may be the word "blister," which is indicative of a pressure injury developed by Patient 4. Upon identifying the keyword 316 in the Note(s) 314, in some cases, the corresponding condition 306 field of the EMR of Patient 4 can be updated to reflect "pressure injury." Further, the condition date 308 of Patient 4 can be updated to reflect the date of the note among the Note(s) 314 that indicated the keyword 316.

In some cases, other parts of the EMRs can be relied upon to identify whether patients have developed pressure injuries or are at risk of developing pressure injuries. For example, the nutrition 310 field of an EMR may be associated with the patient's risk of developing a pressure injury. A low nutrition level, for example, can correlate to a relatively high risk of developing a pressure injury. In a particular example, the nutrition 310 of Patient 4 may be Level 4, which may be relatively low (e.g., below a particular threshold). Based on the nutrition 310 field in the EMR of Patient 4, it may be determined that the risk of Patient 4 for having and/or developing a pressure injury may be relatively high. Examples of nutrition 310 levels that can be tracked in the EMRs and which relate to risks of pressure injuries include levels (e.g., concentrations) of molecules measured in blood, serum, or other bodily fluids (e.g., serum albumin, prealbumin, transferrin, retinal-binding protein, etc.); levels of molecules in food and/or fluids administered to the patients (e.g., calories, protein levels, zinc, Vitamin A, Vitamin C, Vitamin D, arginine, glutamine, etc.); and/or other characteristics of the patients related to nutrition (e.g., hydration levels of the patient, weight changes of the patient, etc.). In various cases, patients can be at risk of pressure injuries if their nutrition 310 levels are too high (e.g., higher than a first threshold) and/or too low (e.g., lower than a second threshold).

In some cases, in response to identifying the keyword 316 and/or a low nutrition 310 level, an alert can be generated indicating the pressure injury of Patient 4 and transmitted to a clinical device associated with a care provider (e.g., a wound care specialist). Thus, automated referrals to care providers can be generated by analyzing the EMRs stored in the datastore 124.

In some cases, the condition date 308 field and the intake date 312 field can be analyzed to determine whether patients developed or were placed at risk of developing pressure injuries in a particular care facility. If the intake date 312 of a particular patient is before the condition date 308 of the particular patient, and the condition of the particular patient includes a pressure injury, then the care facility may be responsible for the pressure injury. For example, Patient 1 has a pressure injury condition 306, an intake date 312 of Jan. 1, 2020, and a condition date 308 of Jan. 5, 2020. Patient 1 developed the pressure injury after entering the care facility, and therefore the care facility may be responsible for the pressure injury of Patient 1. On the other hand, Patient 3 has a pressure injury condition 306, an intake date 312 of Jan. 1, 2020, and a condition date 308 of Dec. 15, 2019. Because the intake date 312 of Patient 3 is after the condition date 308 of Patient 3, the care facility may not be responsible for the pressure injury of Patient 3. In some cases, a report indicating pressure injuries that the care facility is responsible for can be generated. Accordingly, in the example of FIG. 3, the report may omit features of the EMR of Patient 3. Further, the report may omit features of the EMRs of patients without pressure injuries, such as Patient 2, whose condition 306 is a "surgical wound" rather than a pressure injury.

In various examples, alert(s) and/or report(s) can be generated by an identification system (e.g., the identification system 120), an EMR system (e.g., the EMR system 122), or a combination thereof. For example, the identification system and/or the EMR system may analyze the EMRs stored in the datastore 124 to generate alert(s) indicating that one or more patients have pressure injuries or are at risk of developing pressure injuries, to generate report(s) indicating trends associated with pressure injuries developed in a care facility.

Figure 4:
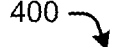
FIG. 4 illustrates an example process for training a computing model to predict a pressure injury based on sensor data and/or EMR data.
Figure 4:
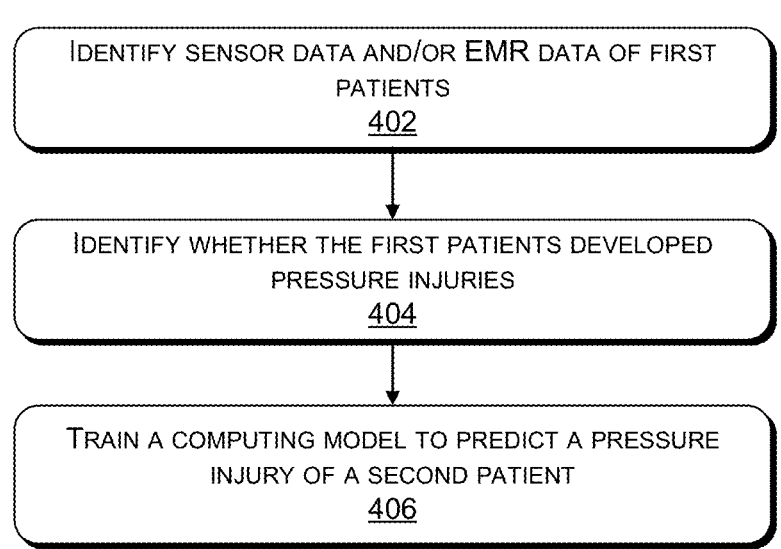

FIG. 4 illustrates an example process 400 for training a computing model to predict a pressure injury based on sensor data and/or EMR data. The process 400 can be performed by an entity including the support device 104, the identification system 120, the EMR system 122, the clinical device 128, or any combination thereof. For example, the process 400 can be performed by one or more computing devices including memory that stores instructions and one or more processors that, when executing the instructions, perform the operations of the process 400.

At 402, the entity can identify sensor data and/or EMR data of first patients. Sensor data may include data indicating one or more parameters of the first patients. The parameter(s) include, for instance, movements of the first patients, moisture of support structures (e.g., beds) of the first patients, nutrition levels of the first patients, temperatures of the first patients, or any other metric relevant to pressure injury susceptibility. In some cases, the sensor data is generated by one or more sensors including load cells configured to detect a pressure of the first patients on support structures (e.g., beds) of the first patients, moisture sensors configured to detect moisture on the support structures, temperature sensors configured to detect temperatures of the first patients, cameras (e.g., infrared cameras, visible light cameras, radar sensors, or some other type of camera) configured to generate infrared images and/or videos of the patient, or any combination thereof.

EMR data may include data stored in EMRs of the first patients. The EMR data may include nutrition levels of the first patients, medical histories of the first patients, notes written by care providers about the first patients, and the like. In some cases, natural language processing can be performed on the notes. For example, one or more keywords associated with pressure injuries or risks of pressure injuries can be identified in the notes.

At 404, the entity can identify whether the first patients developed pressure injuries. In some implementations, the EMR data may indicate one or more of the first patients that developed pressure injuries. For example, the pressure injuries may be indicated as diagnosed conditions within the EMRs of the first patients. In some examples, the pressure injuries may be documented in notes written by care providers about the first patients. The entity, in some cases, may identify one or more keywords in the notes that are indicative of the first patients having pressure injuries.

At 406, the entity can train a computing model to predict a pressure injury of a second patient. The computing model may be a machine learning model, such as a linear regression model, a logistic regression model, a gradient boost machine, a deep learning model, or a combination thereof. In various examples the entity can optimize the computing model based on the sensor data, the EMR data, and indications of whether the first patients developed pressure injuries. For example, one or more factors within the computing model can be optimized such that the computing model accurately predicts whether the first patients developed the pressure injuries based on inputs including the sensor data and the EMR data of the first patients.

Figure 5:
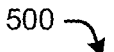
FIG. 5 illustrates an example process for predicting a pressure injury of a patient.
Figure 5:
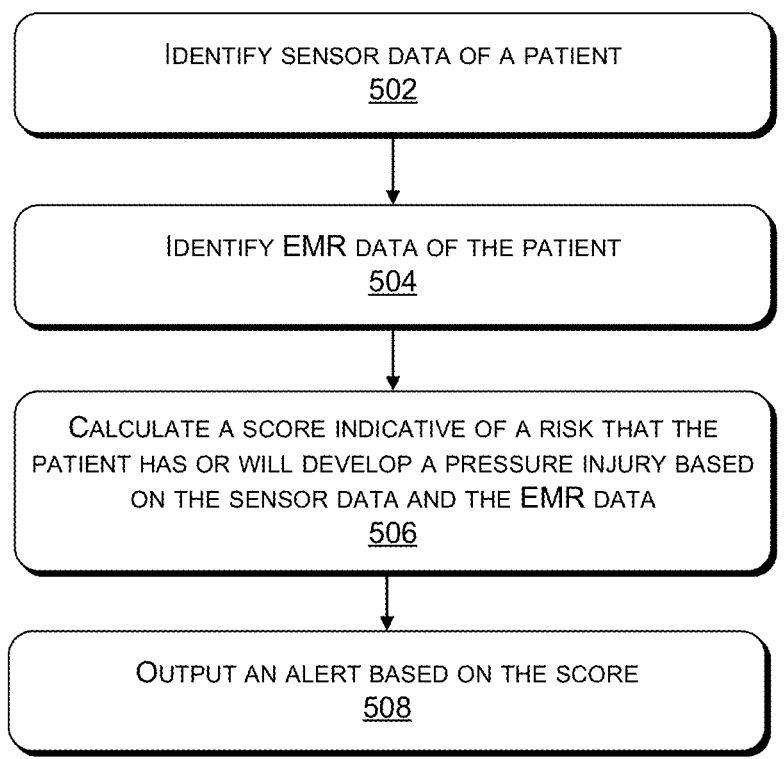

FIG. 5 illustrates an example process 500 for predicting a pressure injury of a patient. The process 500 can be performed by an entity including the support device 104, the identification system 120, the EMR system 122, the clinical device 128, or any combination thereof. For example, the process 500 can be performed by one or more computing devices including memory that stores instructions and one or more processors that, when executing the instructions, perform the operations of the process 500.

At 502, the entity can identify sensor data of the patient. Sensor data may include data indicating one or more parameters of the patient. The parameter(s) include, for instance, movements of the patient, moisture of support structures (e.g., beds) of the patient, nutrition levels of the patient, temperatures of the patient, or any other metric relevant to pressure injury susceptibility. In some cases, the sensor data is generated by one or more sensors including load cells configured to detect a pressure of the patient on the support structure, moisture sensors configured to detect moisture on the support structure, temperature sensors configured to detect temperatures of the patient, cameras (e.g., infrared cameras, visible light cameras, radar sensors, or other types of cameras) configured to generate infrared images and/or videos of the patient, or any combination thereof. The sensors may detect, for instance, parameter(s) at different times and/or different positions with respect to the body of the patient.

At 504, the entity can identify EMR data of the patient. EMR data may include data stored in an EMR of the patient. The EMR data may include nutrition levels of the patient, a medical history of the patient, notes written by care providers about the patient, and the like. In some cases, natural language processing can be performed on the notes. For example, one or more keywords associated with pressure injuries or risks of pressure injuries can be identified in the notes.

At 506, the entity can calculate a score indicative of a risk that the patient has or will develop a pressure injury based on the sensor data and the EMR data. In some cases, the score is calculated by inputting parameters indicated by the sensor data and the EMR data into a computing model, such as an equation or a trained machine learning model. In some cases, the output of the equation or the machine learning model may be the score. In some cases, the score is represented as a percentage corresponding to the risk that the patient has or will develop a pressure injury. In some cases, the score corresponds to a Braden score of the patient. In various implementations, the score indicates that the patient is in danger of developing a pressure injury. For example, the entity determines that the patient has greater than a threshold likelihood (e.g., 50%) of developing a pressure injury within a time period (e.g., a day, a week, etc.).

At 508, the entity can output an alert based on the score. The alert may indicate the risk that the patient has or will develop the pressure injury. In some examples, the alert includes the score. In various examples, the alert indicates that the patient is in danger of developing the pressure injury. The alert, for example, provides an instruction for safe patient handling, providing an improved surface (e.g., placing a cushion, tape, or the like between an object and the patient), consulting an expert (e.g., a WOCN), turning the patient, adding or replacing pads to the support structure of the patient, mobilizing the patient, adjusting nutrition of the patient, modifying an incontinence pad changing schedule, or a combination thereof. According to some implementations, the alert can be output (e.g., pushed) to a computing device associated with a care provider. The alert may instruct the care provider to attend to the patient. Accordingly, the pressure injury may be prevented. In some examples, the score and/or risk may be stored in the EMR of the patient.

Figure 6:
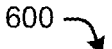
FIG. 6 illustrates another example process for predicting a pressure injury of a patient.
Figure 6:
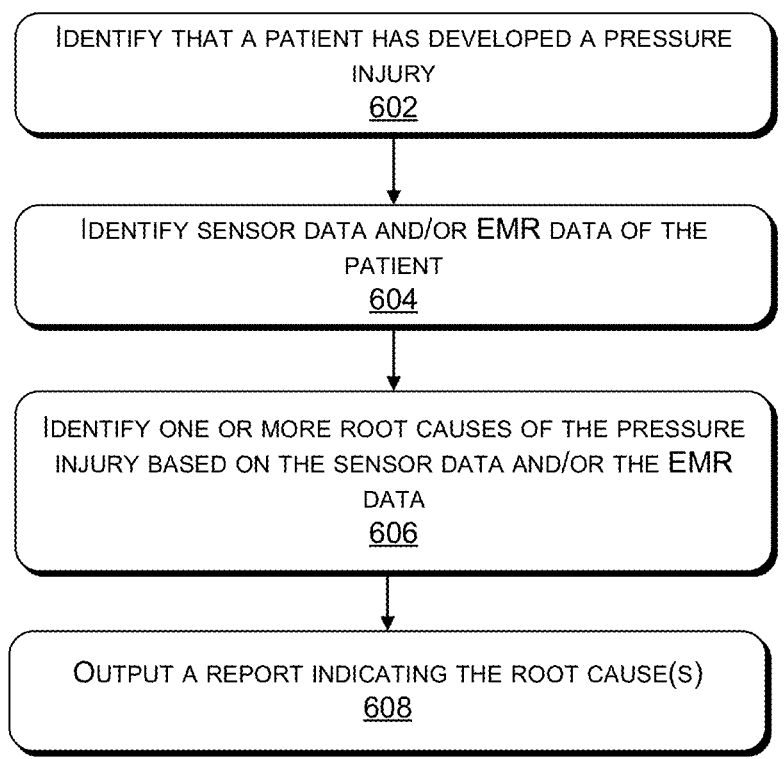

FIG. 6 illustrates an example process 600 for predicting a pressure injury of a patient. The process 500 can be performed by an entity including the support device 104, the identification system 120, the EMR system 122, the clinical device 128, or any combination thereof. For example, the process 600 can be performed by one or more computing devices including memory that stores instructions and one or more processors that, when executing the instructions, perform the operations of the process 600.

At 602, the entity can identify that a patient has developed a pressure injury. In various cases, the entity can identify the pressure injury based on an EMR of the patient. The EMR may be stored in a datastore (e.g., a database). In some cases, the EMR of the patient is stored with EMRs of other patients in the datastore. According to some implementations, the entity can perform natural language processing on at least one note in the EMR of the patient. The entity may identify that the patient has developed the pressure injury if the note(s) include one or more keywords associated with the pressure injury.

At 604, the entity can identify sensor data and/or EMR data of the patient. Sensor data may include data indicating one or more parameters of the patient. The parameter(s) include, for instance, movements of the patient, moisture of support structures (e.g., beds) of the patient, nutrition levels of the patient, temperatures of the patient, or any other type of metric relevant to pressure injury susceptibility. In some cases, the sensor data is generated by one or more sensors including load cells configured to detect a pressure of the patient on the support structure, moisture sensors configured to detect moisture on the support structure, temperature sensors configured to detect temperatures of the patient, cameras (e.g., infrared cameras, visible light cameras, radar sensors, depth cameras, or other types of light sensors) configured to generate images and/or videos of the patient, or any combination thereof. The sensors may detect, for instance, parameter(s) at different times and/or different positions with respect to the body of the patient.

EMR data may include data stored in an EMR of the patient. The EMR data may include nutrition levels of the patient, a medical history of the patient, notes written by care providers about the patient, and the like. In some cases, natural language processing can be performed on the notes. For example, one or more keywords associated with pressure injuries or risks of pressure injuries can be identified in the notes.

At 606, the entity can identify one or more root causes of the pressure injury based on the sensor data and/or the EMR data. In some cases, the root cause(s) include one or more risk factors that the patient experienced prior to the development of the pressure injury. In some cases, these risk factors can be identified based on the sensor data and/or the EMR data. For instance, a parameter indicated by the sensor data and/or the EMR data may be compared to a threshold. Based on the comparison, the entity may conclude that a risk factor associated with the parameter is a root cause of the pressure injury. According to some examples, the entity may conclude that the risk factor is a root cause if the parameter is within a threshold range (e.g., above and/or below a threshold) for greater than a particular time period (e.g., one hour, one day, or some other time period). In some cases, the entity can identify the root cause(s) by inputting the sensor data and/or the EMR data into a trained machine learning model, wherein an output of the trained machine learning model indicates the root cause(s).

At 608, the entity can output a report indicating the root cause(s). According to some examples, the report can indicate the root cause(s) of the pressure injury of the patient as well as root causes of other pressure injuries experienced by other patients in a care facility. Accordingly, the report can indicate trends associated with pressure injuries in the care facility. In some examples, the report can be output to a computing device, such as a computing device associated with an administrator and/or care provider. Using the information contained in the report, the administrator and/or care provider can take efforts to prevent future pressure injuries in the care facility and/or treat the pressure injury of the patient. In some examples, the entity can further update the EMR to indicate the root cause(s) of the patient.

Figure 7:
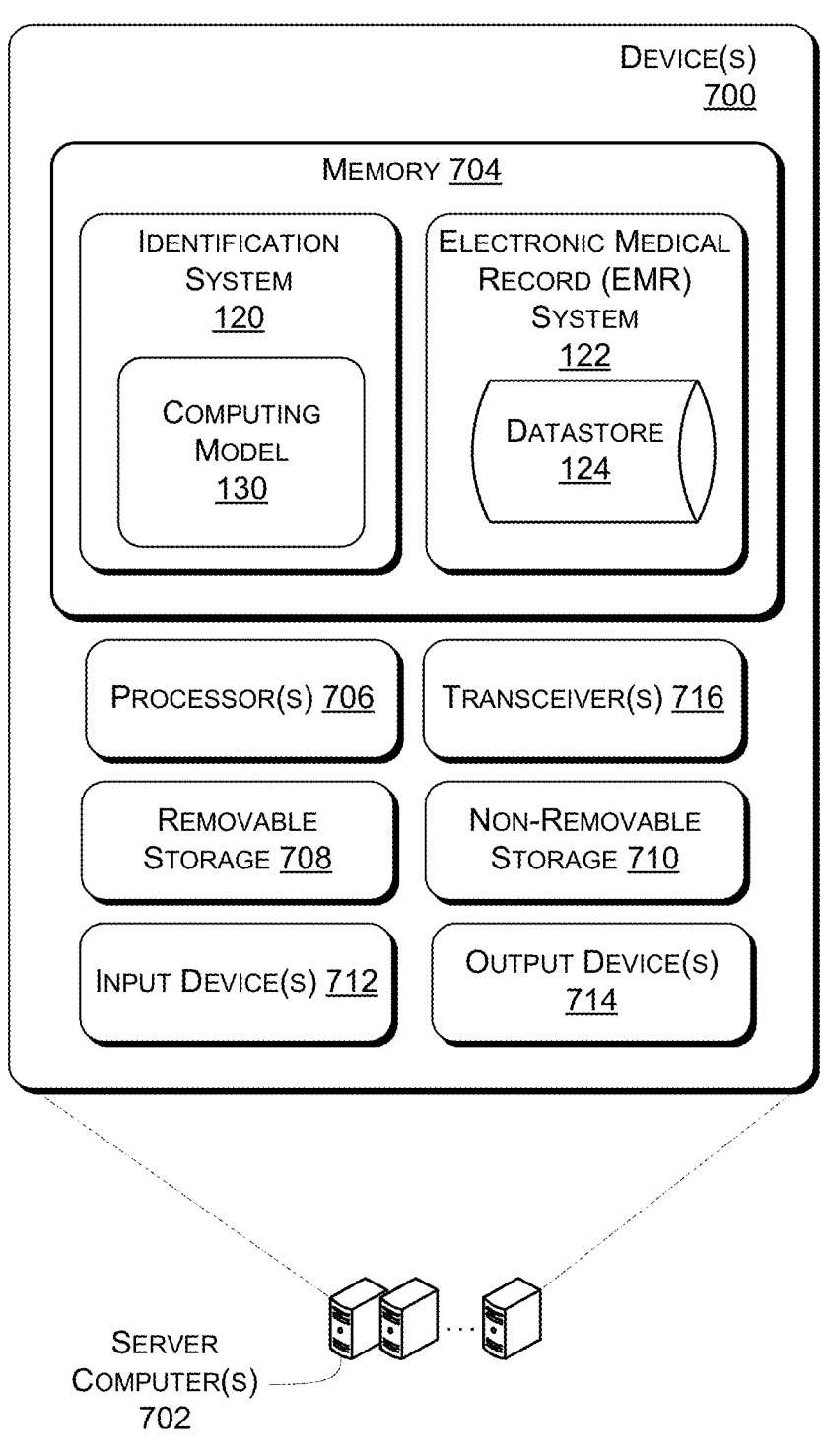
FIG. 7 illustrates at least one example device configured to enable and/or perform the some or all of the functionality discussed herein.

FIG. 7 illustrates at least one example device 700 configured to enable and/or perform the some or all of the functionality discussed herein. Further, the device(s) 700 can be implemented as one or more server computers 702, a network element on a dedicated hardware, as a software instance running on a dedicated hardware, or as a virtualized function instantiated on an appropriate platform, such as a cloud infrastructure, and the like. It is to be understood in the context of this disclosure that the device(s) 700 can be implemented as a single device or as a plurality of devices with components and data distributed among them.

As illustrated, the device(s) 700 comprise a memory 704. In various embodiments, the memory 704 is volatile (including a component such as Random Access Memory (RAM)), non-volatile (including a component such as Read Only Memory (ROM), flash memory, etc.) or some combination of the two.

The memory 704 may include various components, such the identification system 120, the EMR system 122, the datastore 124, the computing model 130, and the like. Any of the identification system 120, the EMR system 122, the datastore 124, the computing model 130 can include methods, threads, processes, applications, or any other sort of executable instructions. The identification system 120, the EMR system 122, the datastore 124, the computing model 130 and various other elements stored in the memory 704 can also include files and databases.

The memory 704 may include various instructions (e.g., instructions the identification system 120, the EMR system 122, the datastore 124, and/or the computing model 130), which can be executed by at least one processor 706 to perform operations. In some embodiments, the processor(s) 706 includes a Central Processing Unit (CPU), a Graphics Processing Unit (GPU), or both CPU and GPU, or other processing unit or component known in the art.

The device(s) 700 can also include additional data storage devices (removable and/or non-removable) such as, for example, magnetic disks, optical disks, or tape. Such additional storage is illustrated in FIG. 7 by removable storage 708 and non-removable storage 710. Tangible computer-readable media can include volatile and nonvolatile, removable and non-removable media implemented in any method or technology for storage of information, such as computer readable instructions, data structures, program modules, or other data. The memory 704, removable storage 708, and non-removable storage 710 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 700. Any such tangible computer-readable media can be part of the device(s) 700.

The device(s) 700 also can include input device(s) 712, such as a keypad, a cursor control, a touch-sensitive display, voice input device, etc., and output device(s) 714 such as a display, speakers, printers, etc. These devices are well known in the art and need not be discussed at length here. In particular implementations, a user can provide input to the device(s) 700 via a user interface associated with the input device(s) 712 and/or the output device(s) 714. In some cases, the input device(s) 712 include one or more sensors, such as the load cell(s) 106, the moisture sensor(s) 108, the temperature sensor(s) 110, the camera(s) 112, the video camera(s) 114, or any combination thereof.

As illustrated in FIG. 7, the device(s) 700 can also include one or more wired or wireless transceiver(s) 716. For example, the transceiver(s) 716 can include a Network Interface Card (NIC), a network adapter, a LAN adapter, or a physical, virtual, or logical address to connect to the various base stations or networks contemplated herein, for example, or the various user devices and servers. To increase throughput when exchanging wireless data, the transceiver(s) 716 can utilize Multiple-Input/Multiple-Output (MIMO) technology. The transceiver(s) 716 can include any sort of wireless transceivers capable of engaging in wireless, Radio Frequency (RF) communication. The transceiver(s) 716 can also include other wireless modems, such as a modem for engaging in Wi-Fi, WiMAX, Bluetooth, or infrared communication.

In some implementations, the transceiver(s) 716 can be used to communicate between various functions, components, and modules that are comprised in the device(s) 700. For instance, the transceivers 716 may facilitate communications between the identification system 120, the EMR system 122, the datastore 124, the computing model 130, and the like. In some cases, the transceiver(s) 716 include the transmitter 116.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

Although the subject matter has been described in language specific to structural features and/or methodological acts, it is to be understood that the subject matter defined in the appended claims is not necessarily limited to the specific features or acts described.

EXAMPLE CLAUSES

1. A pressure injury identification system, including: a bed configured to support a patient; one or more sensors coupled to the bed and configured to detect one or more parameters of the patient, and to generate sensor data based on the one or more parameters; a transceiver; at least one processor operably connected to the transceiver and the one or more sensors; and memory operably connected to the at least one processor, the memory storing: a database including an electronic medical record (EMR) of the patient; and instructions that, when executed by the at least one processor, cause the at least one processor to perform operations including: determining, based on the EMR of the patient, that the patient has a pressure injury; determining, based on the sensor data, at least one root cause of the pressure injury; updating the EMR to indicate the at least one root cause of the pressure injury; and causing the transceiver to output, to an external computing device, a report indicating the pressure injury and the at least one root cause of the pressure injury.

2. The pressure injury identification system of clause 1, wherein the one or more sensors includes at least one of a load cell configured to detect a pressure of the patient on the bed, a moisture sensor configured to detect moisture on the bed, a temperature sensor configured to detect a temperature of the patient, an infrared camera configured to generate at least one infrared image of the patient, or a video camera configured to generate at least one video of the patient.

3. The pressure injury identification system of clause 1 or 2, wherein determining the at least one root cause of the pressure injury includes: determining a time at which the EMR was updated to indicate the pressure injury; determining, based on the sensor data, that the patient experienced a risk factor associated with the pressure injury prior to the time at which the EMR was updated to indicate the pressure injury; and determining the at least one root cause based on the risk factor.

4. A method, including: determining, based on an electronic medical record (EMR) of a patient, that the patient has an injury; receiving, from one or more sensors, sensor data indicating one or more parameters of the patient; determining, based on the sensor data, at least one root cause of the injury; and transmitting, to an external computing device, a report indicating the injury and the at least one root cause of the injury.

5. The method of clause 4, wherein determining that the patient has the injury includes: identifying a note in the EMR of the patient; and identifying, in the note, at least one keyword associated with the injury.

6. The method of clause 4 or 5, wherein the one or more sensors are in a bed supporting the patient, the one or more sensors including at least one of a load cell, a moisture sensor, a temperature sensor, an infrared camera, or a video camera.

7. The method of any one of clauses 4 to 6, wherein the one or more parameters of the patient include at least one of a movement of the patient, a moisture of a bed supporting the patient, a nutrition level of the patient, or a temperature of the patient.

8. The method of any one of clauses 4 to 7, wherein determining the at least one root cause of the injury includes: determining that the one or more parameters are within one or more threshold ranges for greater than one or more time periods.

9. The method of any one of clauses 4 to 8, wherein determining the at least one root cause of the injury includes: inputting the sensor data into a trained machine learning model; and determining the at least one root cause of the injury based on an output of the trained machine learning model.

10. The method of any one of clauses 4 to 9, further including: determining, based on the EMR of the patient, a nutrition level of the patient, wherein determining the at least one root cause of the injury includes: determining that the nutrition level of the patient has remained under a threshold level for greater than a time period; and determining that the nutrition level of the patient is an additional root cause of the injury.

11. The method of any one of clauses 4 to 10, wherein determining the at least one root cause of the pressure injury includes: determining a time at which the EMR was updated to indicate the pressure injury; determining, based on the sensor data, that the patient experienced a risk factor associated with the pressure injury prior to the time at which the EMR was updated to indicate the pressure injury; and determining the at least one root cause based on the risk factor.

12. The method of any one of clauses 4 to 11, the patient being a first patient, the injury being a first injury, the EMR being a first EMR, the method further including: identifying, based on second EMRs of second patients, that the second patients have second injuries; determining that the second injuries have the same type of root cause; and transmitting, to an external computing device, a report indicating the type of root cause of the second injuries.

13. A system, including: at least one processor; and memory operably connected to the at least one processor, the memory storing instructions that, when executed by the at least one processor, cause the at least one processor to perform operations including: receiving, from one or more sensors, sensor data indicating one or more parameters of the patient, the one or more sensors including a camera, the sensor data including images of the patient over a time period; predicting, based on the sensor data, that the patient is in danger of acquiring a pressure injury; updating an electronic medical record (EMR) of the patient to indicate the pressure injury; and transmitting, to an external computing device, an alert indicating that the patient is in danger of acquiring the pressure injury.

14. The system of clause 13, wherein the one or more sensors are included in a bed supporting the patient, the one or more sensors at least one of a load cell, a pressure sensor, a sensing pad, a moisture sensor, or a temperature sensor, and wherein the camera includes an infrared camera, a depth-sensing camera, or a video camera.

15. The system of clause 13 or 14, wherein the one or more parameters of the patient include a movement of the patient indicated by the images.

16. The system of any one of clauses 13 to 15, wherein the one or more parameters of the patient include at least one of a moisture of a bed supporting the patient, a nutrition level of the patient, or a temperature of the patient.

17. The system of any one of clauses 13 to 16, wherein determining that the patient is in danger of acquiring the pressure injury includes: calculating a pressure injury score based on the one or more parameters, the pressure injury score corresponding to a likelihood that the patient will acquire the pressure injury; and determining that the pressure injury score exceeds a threshold.

18. The system of any one of clauses 13 to 17, wherein determining that the patient is in danger of acquiring the pressure injury includes: inputting the sensor data into a trained machine learning model; and determining that the patient is in danger of acquiring the pressure injury based on an output of the trained machine learning model.

19. The system of any one of clauses 13 to 18, wherein the operations further include: determining, based on the EMR of the patient, a nutrition level of the patient, and wherein determining that the patient is in danger of acquiring the pressure injury further includes: determining that the nutrition level of the patient was below a threshold for greater than a time period.

20. The system of any one of clauses 13 to 19, wherein the operations further include: determining that the patient has acquired the pressure injury; and determining, based on the sensor data, at least one root cause of the pressure injury, and wherein the report further indicates the at least one root cause of the pressure injury.

21. The system of any one of clauses 13 to 20, wherein predicting, based on the sensor data, that the patient is in danger of acquiring a pressure injury includes predicting that a body part of the patient is in danger of acquiring the pressure injury, and wherein the alert indicates that the body part of the patient is in danger of acquiring the pressure injury.

22. The system of any one of clauses 13 to 21, wherein the alert further indicates one or more recommended interventions associated with reducing a risk that the patient will acquire the pressure injury.

23. A system, including: at least one processor; and memory operably connected to the at least one processor, the memory storing instructions that, when executed by the at least one processor, cause the at least one processor to perform operations including: receiving, from sensors, sensor data indicating one or more parameters of multiple patients in a unit, the sensors including one or more cameras, the sensor data including images of the patients over a time period; predicting, based on the sensor data, that a number of the patients are in danger of acquiring pressure injuries; generating an alert based on the number of the patients that are in danger of acquiring the pressure injuries, the alert including a recommended intervention that includes at least one of an instruction to assign staff to the unit or to provide equipment to the unit; and transmitting, to an external computing device, the alert.

The invention claimed is:

1. An automatic pressure injury identification system, comprising:

a bed configured to support a patient;

the bed comprising one or more sensors configured to detect one or more parameters of the patient, and to generate sensor data from the detection of the one or more parameters, wherein the sensors are contact-free continuous monitoring sensors selected from pressure sensors, moisture sensors, temperature sensors, and cameras;

a transceiver;

at least one processor operably connected to the transceiver and the one or more sensors; and memory operably connected to the at least one processor, the memory storing:

a database comprising an electronic medical record (EMR) of the patient; and instructions that, when executed by the at least one processor, cause the at least one processor to perform operations comprising:

determining, based on the EMR of the patient, that the patient has a pressure injury;

identifying sensor data, from one or more sensors, obtained prior to a time at which the EMR was updated to indicate the pressure injury, the sensor data indicating one or more parameters of the patient;

determining at least one root cause of the pressure injury, wherein determining the at least one root cause of the pressure injury comprises:

determining the time at which the EMR was updated to indicate the pressure injury, determining, using an output from a machine learning model input with the sensor data indicating the one or more parameters of the patient, that the patient experienced at least one risk factor associated with the pressure injury, wherein the machine learning model is trained using sensor data and EMR data:

prior to the time at which the EMR was updated, and for greater than a threshold period of time; and determining, based on the EMR, that the patient experienced the at least one risk factor prior to the time at which the EMR was updated;

electronically updating the EMR to indicate the at least one root cause of the pressure injury; and causing the transceiver to output, to an external computing device, a report indicating the pressure injury and the at least one root cause of the pressure injury.

2. The pressure injury identification system of claim 1, wherein the contact-free continuous monitoring sensors are configured to detect a pressure of the patient on the bed, detect moisture on the bed, detect a temperature of the patient, generate at least one infrared image of the patient, or generate at least one video of the patient.

3. The identification system of claim 1, wherein the risk factor is a condition of the patient, the condition of the patient comprising patient diagnosis and/or current medication.

4. The identification system of claim 1, wherein the pressure sensors are load cells located at each corner of a resting surface of the bed.

5. A method, comprising:

receiving, from one or more sensors, sensor data indicating one or more parameters of a patient;

determining, based on an electronic medical record (EMR) of the patient, that the patient has a pressure injury;

determining, based on the sensor data indicating the one or more parameters of the patient, at least one root cause of the pressure injury, wherein determining the at least one root cause of the pressure injury comprises:

determining a time at which the EMR was updated;

inputting the sensor data and the EMR data into a trained machine learning model; and determining, based on the sensor data indicating the one or more parameters of the patient and an output of the trained machine learning model, that the patient experienced a risk factor associated with the pressure injury prior to the time at which the EMR was updated;

determining an estimated contribution of a potential root cause to the pressure injury of the patient; and transmitting, to an external computing device, a report indicating the pressure injury and the estimated contribution of the associated at least one root cause of the pressure injury.

6. The method of claim 5, wherein determining that the patient has the injury comprises:

identifying a note in the EMR of the patient; and identifying, in the note, at least one keyword associated with the injury via natural language processing.

7. The method of claim 6, wherein the one or more sensors are in a bed supporting the patient, the one or more sensors comprising at least one of a load cell, a moisture sensor, a temperature sensor, an infrared camera, or a video camera, and wherein the one or more parameters of the patient comprise at least one of a movement of the patient, a moisture of a bed supporting the patient, a nutrition level of the patient, or a temperature of the patient.

8. The method of claim 6, wherein determining the at least one root cause of the injury comprises:

determining that the one or more parameters are within one or more threshold ranges for greater than one or more time periods.

9. The method of claim 6, further comprising:

determining, based on the EMR of the patient, a nutrition level of the patient, wherein determining the at least one root cause of the injury further comprises:

determining that the nutrition level of the patient has remained under a threshold level for greater than a time period; and determining that the nutrition level of the patient is an additional root cause of the injury.

10. The method of claim 6, the patient being a first patient, the injury being a first injury, the EMR being a first EMR, the method further comprising:

identifying, based on second EMRs of second patients, that the second patients have second injuries;

determining, based on the sensor data, that the second patients experienced a second risk factor associated with a pressure injury, wherein the second risk factor is a same risk factor as the risk factor of the first patient;

determining in real-time that the second injuries have the same type of root cause as the first injury of the first patient; and transmitting, to an external computing device, a report indicating the type of root cause of the second injuries and a treatment plan.

11. The method of claim 6, the patient being a first patient, the injury being a first injury, and the EMR being a first EMR, the method further comprising:

predicting, based on a second EMR of a second patient, that the second patient is at risk for developing second injuries based on a same type of root cause as the first patient; and transmitting, to an external computing device in real time, a report indicating the risk of the second patient developing the second injury.

\* \* \* \* \*